(12) United States Patent
Kushwaha et al.

(10) Patent No.: US 6,988,417 B2
(45) Date of Patent: Jan. 24, 2006

(54) DISPLACEMENT AND FORCE SENSOR

(75) Inventors: R. Lal Kushwaha, Saskatoon (CA); Louis Roth, Saskatoon (CA); James Schnaider, Barthel (CA); Tyrel Lloyd, Unity (CA); William C. Roberts, Medicine Hat (CA); Wayne Morley, Saskatoon (CA); Denise Stilling, Saskatoon (CA)

(73) Assignee: University of Saskatchewan, Saskatshewan (CA)

( * ) Notice: Subject to any disclaimer, the term of this patent is extended or adjusted under 35 U.S.C. 154(b) by 108 days.

(21) Appl. No.: 10/670,441

(22) Filed: Sep. 25, 2003

(65) Prior Publication Data

US 2004/0149044 A1    Aug. 5, 2004

Related U.S. Application Data

(60) Provisional application No. 60/414,406, filed on Sep. 30, 2002.

(51) Int. Cl.
*G01N 3/02* (2006.01)
(52) U.S. Cl. ............................ 73/856; 73/847; 73/852; 73/853
(58) Field of Classification Search ................. 73/847, 73/852, 853, 856
See application file for complete search history.

(56) References Cited

U.S. PATENT DOCUMENTS

| | | | | | |
|---|---|---|---|---|---|
| 4,196,618 | A | * | 4/1980 | Patterson | 73/149 |
| 4,266,878 | A | * | 5/1981 | Auer | 356/419 |
| 5,269,190 | A | * | 12/1993 | Kramer et al. | 73/822 |
| 5,305,634 | A | * | 4/1994 | Suga et al. | 73/86 |
| 2003/0188585 | A1 | * | 10/2003 | Esser et al. | 73/826 |

* cited by examiner

*Primary Examiner*—Alandra Ellington
(74) *Attorney, Agent, or Firm*—Schwartz Law Firm P.C.

(57) ABSTRACT

An apparatus for measuring the displacement of visco-elastoplastic media below a surface thereof comprises an upper plate mounted such that a displacement force exerted on the top surface thereof will move the upper plate a displacement distance downward toward a base. Guides maintain the upper plate and the base in alignment such that movement is along a displacement axis. A calibrated bias element exerts a calibrated bias force resisting movement of the upper plate toward the base. A displacement measuring device measures the displacement distance, and is operative to generate a movement signal corresponding to the displacement distance. A data acquisition system is operative to receive and record the movement signal, and calculate the displacement force exerted on the top surface of the upper plate required to move the upper plate the displacement distance against the calibrated bias force.

19 Claims, 5 Drawing Sheets

DISPLACEMENT AND FORCE SENSOR

The present invention relates to a device for conveniently measuring displacement profiles beneath the surface of particulate or visco-elastoplastic media such as soils, in response to forces transferred through and in the media.

BACKGROUND OF THE INVENTION

Measuring actual displacement at various depths below the surface of an area of soil in response to forces exerted on the surface is conventionally difficult and time consuming. Conventionally, an indicator, such as a flexible film or a layer of powder, is placed between layers of soil. The desired load or force is applied to the soil surface, and the soil is excavated and displacement of the indicators is measured.

Such a process requires that soil be excavated from a hole and the soil placed back in the hole with indicators between layers. In a lab setting, soil and indicators can be layered in a box.

Soils are complex media comprising particulate solids, liquids and gases that can be modeled as visco-elastoplastics. It is known that soil displacement in response to a surface load is greater near the surface, and reduces to zero at some depth below the surface. The distribution of soil deflection beneath the soil surface resulting from a surface applied force has not been accurately measured.

It is often assumed, for practical purposes, that observed surface deflections are cumulative effects of subsurface compactions, however, it is known that soil dynamic characteristics vary with soil composition and depth and are nonlinear. Soil characteristics vary widely among locations.

Conventional technology utilizes load cells and customized piezoelectric tape sensors, to measure the force exerted at various depths in a soil as a result of a force applied to the soil surface. Deflection of soil beneath the surface is measured typically from the surface impression, assumed to represent cumulative displacement. For many purposes this may be a sufficiently accurate assumption, however for other purposes, a more accurate measurement of subsurface soil displacement would be desirable.

Further, using previously available technology, temporal displacement and force history is not obtainable. Thus the available procedures for displacement measurements are slow, labor intensive, and inaccurate, and there is no known method of measuring soil displacement over time. An improved device for measuring the displacement of soil, and the timing of that displacement, in response to a surface force would be useful, for example, in developing equipment for clearing landmines from an area. A frequent consequence of armed conflicts is the deployment of landmines in soils of affected countries or regions of countries. Large numbers of such landmines remain in large tracts of land after the cessation of armed conflicts. The location of individual landmines within such tracts is almost always indeterminate.

Inadvertent detonation of landmines in former conflict regions causes injury and death daily. Landmines are a major socioeconomic factor that adversely affects countries' abilities to recover from the effects of armed conflict. The presence of landmines at unknown locations in soils disrupts normal trade and commercial activities, access to schools, social services, water and land resources, and other services, and resources sought by people.

Landmines comprise an explosive material and means to trigger detonation of the explosive material. Most landmines are known to be detonated by a certain quantum of downward displacement of an upper structure of a landmine relative to at least one other structure of the landmine. Typically a bias element resists the downward movement of the upper structure, providing a force that must be overcome to cause the displacement necessary to trigger the mine. Such downward displacement can trigger detonation of the explosive material by a variety of known means. Most landmines are designed to be buried in soil such that the downward displacement occurs consequent to the application of a force to the surface of the soil above the deployment site which causes downward displacement of the soil subjected to that force, and translation of that force and such downward displacement of soil to the upper structure of the landmine.

Most deployed landmines are designed to be detonated by either: (a) people (antipersonnel mines); (b) vehicles weighing less than tanks (antivehicle mines); or (c) tanks (antitank mines). Such landmine types differ in that the force required to be overcome to cause a triggering displacement of the upper structure of an antitank mine is greater than the force required to cause triggering displacement of an antivehicle mine's upper structure, which is, in turn, greater that the force required to cause triggering displacement of an antipersonnel mine's upper structure. The range of forces necessary to cause such displacements in landmines of all three types, as produced by a variety of manufacturers, is known.

Usually, forces exerted to the surfaces of soils by people stepping thereon are insufficient to cause detonation of the explosive materials of antitank or antivehicle mines. Also, it is known that antitank and antivehicle mines typically comprise sufficient masses of metallic structures to permit detection of such landmines by known remote metal-detection means whereas many antipersonnel mines comprise little metallic mass and cannot be detected efficiently by such means. Antipersonnel mines typically contain lesser amount of explosive materials that the other landmine types. However, the number of antipersonnel mines deployed far exceeds the number of antivehicle and antitank mines combined, and the preponderance of death, injury, and other loss caused by inadvertent landmine detonations is attributable to antipersonnel mines.

Current efforts to reclaim tracts of land containing or suspected to contain landmines commonly involves detonating landmines by applying force to soil-surface sites sufficient to cause detonation of landmine explosive materials in situ, or sufficient to damage landmine trigger means in situ so as to render the trigger means inoperable. It is preferable that the explosive materials be detonated in situ. Such efforts employ, for example, high-impact flailing hammer mechanisms to strike soil-surface sites.

To detonate a landmine, enough force must be applied to the soil surface to cause translation through the soil of both a sufficient force and a sufficient downward displacement of soil to sufficiently displace the upper structure of the landmine. Thus in compacted soil conditions a force may be translated to the landmine, however the compacted soil does not move, and so the upper structure of the landmine is not displaced, and the landmine remains operational in the soil. Similarly in very loose soils the surface force may be dissipated through the soil prior to reaching the landmine, with the result that there is not sufficient force on the upper structure to overcome the resisting bias force and displace the upper structure. In some cases the loose soil may actually flow around the landmine—there is sufficient displacement but insufficient force. In such conditions a higher force may be required to detonate the landmines than in more typical soil in the same area. For safe and effective antipersonnel mine detonation it would be desirable to determine the forces required to be applied to the surface of soils in particular locations that are sufficient to detonate antipersonnel mines, but insufficient to detonate other mine types. Quantifying the displacement and force pattern within the soil is required and since the applied load or impact from the landmine-detonation device is known to be dynamic, temporal displacement and force patterns should be measured. Compared to the landmine-detonation devices, the feet of a walking person exert a lesser and varying force for a longer period of time. The soil displacement under the soil surface is related to the force exerted and the length of time for which it is exerted on an area of soil surface. Dynamic loading comparisons between the landmine-detonation device and a walking person can be used more accurately to predict the efficacy of the detonation device.

As discussed above, present technology does not provide for convenient measurement of soil displacement and forces over time. Furthermore, such known devices as load cells for measuring force alone are expensive and can be easily damaged by the large magnitude impulse forces exerted by landmine detonating equipment.

Therefore, it would be desirable to have available technology for an in situ measurement of soil temporal displacement and force translation patterns related to site-specific soil deformation characteristics. Ideally, such technology would be robust and of low cost.

An improved device for measuring the displacement of soil would also be useful in measuring the effects of agricultural practices on soil. Heavy equipment operating over the soil surface can cause changes in soil dynamic characteristics, including the formation of subsurface compaction that can affect water retention capacity, penetrability, and other characteristics related to agricultural yields.

Similarly such a subsurface displacement measuring device could be useful in studying other visco-elastoplastic media such as snow, to measure displacement in mountain snowpack, glaciers and the like.

SUMMARY OF THE INVENTION

It is an object of the present invention to provide an apparatus for measuring the displacement of particulate or visco-elastoplastic media, such as soils, beneath the surface thereof in response to a force exerted thereon that overcomes problems in the prior art. It is a further object of the present invention to provide such an apparatus that is sensitive, reliable and relatively low cost for sensing and measuring force and displacement time profiles in varying conditions of particulate or visco-elastoplastic media such as soils, at various depths and under various loading conditions.

It is a further object of the present invention to provide a device useful to determining physical parameters of soils, applicable to the design of safe and effective programs for detonation of landmines in situ.

The invention provides, in one embodiment, an apparatus for measuring the displacement of, and force on, visco-elastoplastic media below a surface thereof. The apparatus comprises an upper plate having a top surface and mounted in the apparatus such that a displacement force exerted on the top surface will move the upper plate a displacement distance downward toward a base. Guides are operative to maintain the upper plate and the base in alignment such that movement of the upper plate toward the base is along a displacement axis. A calibrated bias element is operative to exert a calibrated bias force resisting movement of the upper plate toward the base. A displacement measuring device is operative to measure the displacement distance moved by the upper plate towards the base, and is operative to generate a movement signal corresponding to the displacement distance. A data acquisition system is operative to receive and record the movement signal, and operative to calculate the displacement force exerted on the top surface of the upper plate required to move the upper plate the displacement distance against the calibrated bias force.

In a second embodiment the invention provides a method of measuring the displacement of, and force on, visco-elastoplastic media below a surface thereof. The method comprises providing an upper plate having a top surface, and a base located at a desired depth under the surface of the visco-elastoplastic media; orienting the upper plate relative to the base such that a displacement force exerted on the top surface will move the upper plate a displacement distance downward toward the base; with guides, maintaining the upper plate and the base in alignment such that movement of the upper plate toward the base is along a displacement axis; providing a calibrated bias element operative to exert a calibrated bias force resisting movement of the upper plate toward the base; exerting a load force on the visco-elastoplastic media and measuring the displacement distance moved by the upper plate towards the base in response to the load force; and recording the displacement distance, and calculating the displacement force exerted on the top surface of the upper plate required to move the upper plate the displacement distance against the calibrated bias force.

The apparatus can sense relative displacement of the upper plate with respect to the base. Where the device is scaled so as to emulate the dimensions of a landmine, knowledge of such displacement, and knowledge of the quantum of force translated to the upper plate can be useful. Where the device is not so scaled and for purposes of determining the absolute quantum of force translated along the axis of displacement allowed between the upper plate and base, for example, for studying subsurface compaction that can affect water retention capacity, penetrability, and other characteristics related, directly or indirectly to agricultural yields from the utility of soils, an accelerometer can be attached to the base.

To measure relative or absolute soil displacement and translated force in the permitted planes of the outer surface of the upper plate an apparatus is inserted into a particulate or visco-elastoplastic medium such as soil and subjected to loading by applying to the medium a force at a location distant from the apparatus. A voltage applied to the Hall effect transducer coupled with a relative displacement between the upper plate and the base will cause an output voltage to fluctuate in relation to the quantum of the displacement. Where an accelerometer is employed, a change in the velocity of the lower plate with cause an output voltage to fluctuate in relation to the quantum of the said change of velocity.

DESCRIPTION OF THE DRAWINGS

While the invention is claimed in the concluding portions hereof, preferred embodiments are provided in the accompanying detailed description which may be best understood in conjunction with the accompanying diagrams where like parts in each of the several diagrams are labeled with like numbers, and where:

DETAILED DESCRIPTION OF THE ILLUSTRATED EMBODIMENTS

Figure 1:
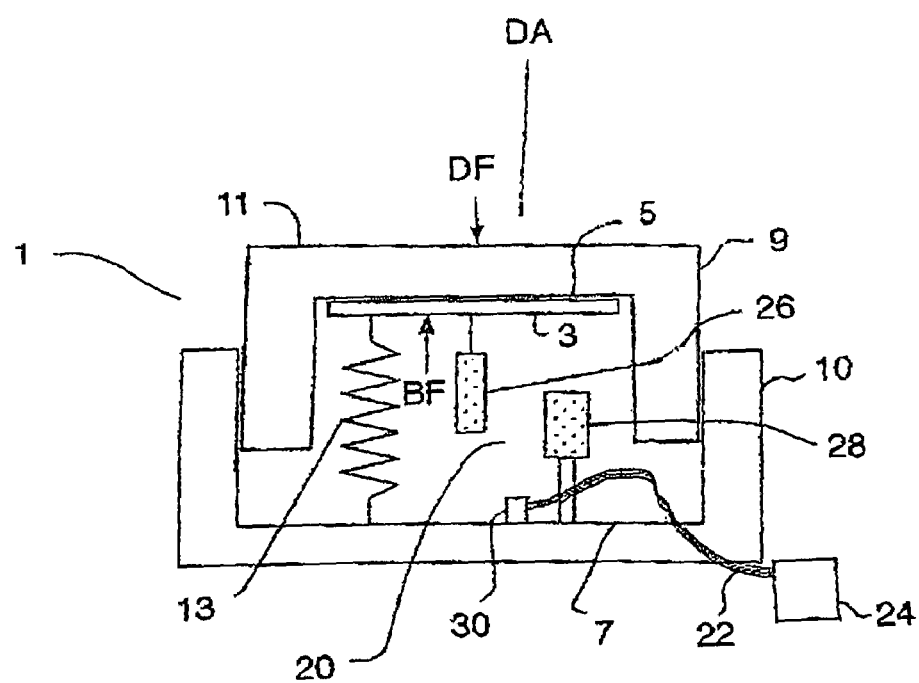
FIG. 1 is a schematic side view of an apparatus of the invention.

FIG. 1 schematically illustrates an apparatus 1 of the invention for measuring the displacement of visco-elastoplastic media, such as soils, below the surface thereof. The apparatus 1 comprises an upper plate 3 having a top surface 5 and mounted in the apparatus 1 such that a displacement force DF exerted on the top surface 5 will move the upper plate 3 a displacement distance downward toward a base 7. To enclose and protect the sensing components, the apparatus 1 includes a casing assembly comprising an upper casing member 9 telescoping with respect to a lower casing member 10. The upper plate 3 is fixed to the upper casing member 9 such that a force DF exerted on the top surface 11 of the upper casing member 9 is directly transferred to the top surface 5 of the upper plate 3 and thus pushes the upper plate downward toward the base 7. In the illustrated embodiment the lower casing member 10 also provides the base 7.

In addition to enclosing and protecting the sensing components of the apparatus 1, the telescoping upper and lower casing members 9, 10 also act as guides operative to maintain the upper plate 3 and the base 7 in alignment such that movement of the upper plate 3 toward the base 7 is confined along a displacement axis DA that is parallel to the walls of the casing members 9, 10. The casing assembly forms an interface between the visco-elastoplastic media, such as soil, and the sensing components.

A calibrated bias element, illustrated in FIG. 1 as a spring 13, is operative to exert a calibrated bias force BF resisting movement of the upper plate 3 toward the base 7. The spring 13 has a known spring constant such that the displacement force DF required to move the upper plate 3 through the displacement distance toward the base 3 can be calculated.

A displacement measuring device 20 is operative to measure the displacement distance moved by the upper plate 3 towards the base 7, and generates a movement signal corresponding to the displacement distance that is transmitted through a wiring harness 22 to a data acquisition system 24. The data acquisition system 24 is operative to receive and record the movement signal, and calculate the displacement force DF exerted on the top surface 5 of the upper plate 3 required to move the upper plate 3 the displacement distance against the calibrated bias force BF.

In the illustrated embodiment of FIG. 1, the displacement measuring device 20 is a Hall effect displacement measuring assembly comprising a magnet 26 fixed to the upper plate 3 and a Hall effect transducer 28 fixed to the base 7. A supply voltage for operating the Hall effect displacement measuring assembly is also carried through the wiring harness 22. The Hall effect displacement measuring assembly is economical and rugged, as described more particularly below, and is well suited to distance measurement in the apparatus of the present invention, although other measuring mechanisms such as proximity transducers, linear voltage displacement transducers, and the like could be utilized as well.

The embodiment of FIG. 1 further comprises an accelerometer 30 attached to the base 7. The accelerometer 30 is operative to measure movement along the displacement axis DA of the base 7 with respect to the visco-elastoplastic media in which it rests. The measurement of movement of the base 7 provides further information on the dynamics of the soil under a load force. The displacement measuring device 20 provides measurement of movement of the upper plate 3 with respect to the base 7. This information is sufficient to simulate a landmine for testing landmine detonation equipment, however for studying the visco-elastoplastic media itself, it could be desirable to further determine the absolute movement of the apparatus 1 relative to the media. This information is provided by the accelerometer 30.

Figure 2:
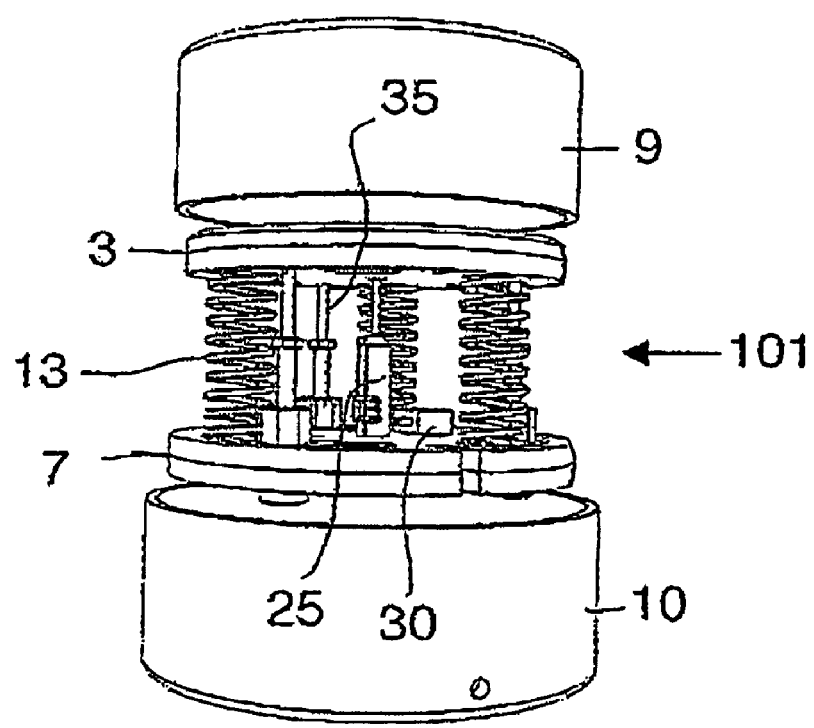
FIG. 2 is a perspective view of an embodiment of the invention
Figure 3:
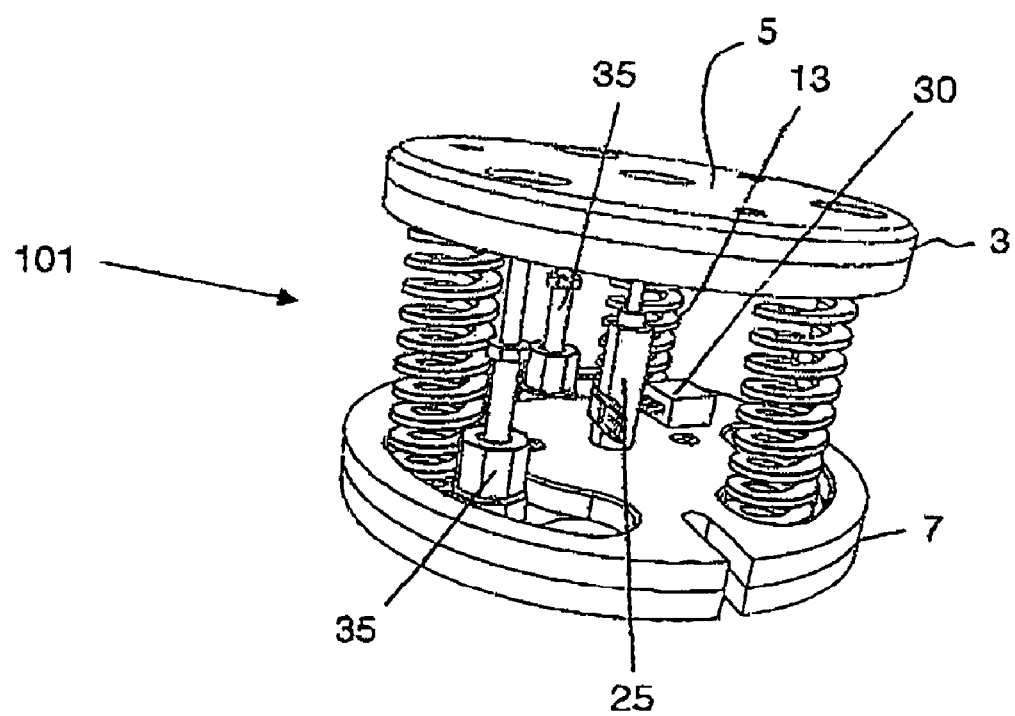
FIG. 3 is a perspective view of the embodiment of FIG. 2 with the casing members removed.

FIGS. 2 and 3, show a physical apparatus 101 of the invention comprising an upper plate 3 with a top surface 5, base 7, springs 13, a Hall effect displacement measuring assembly 25, and an accelerometer 30. In the illustrated embodiment the upper plate 3 comprises two planar pieces that are be fixedly attached to each other with screws or the like. The base 7 is similarly made up of two planar pieces. Such a construction facilitates assembly of the apparatus 101. The apparatus 101 also illustrates a displacement limiting assembly 35 operative to limit the displacement distance that the upper plate can move down, thereby protecting the apparatus from excessive load forces. The springs 13 can be changed to vary the bias force BF and change the operating range of the apparatus 101. The length of the displacement limiting assembly 35 can also be adjusted as required.

FIG. 2 also illustrates telescoping upper and lower casing members 9, 10 which enclose and protect the working parts of the apparatus 101, as well as guide the movement of the upper plate 3 with respect to the base 7 so that such movement is parallel with the walls of the casing members 9, 10.

Figure 4:
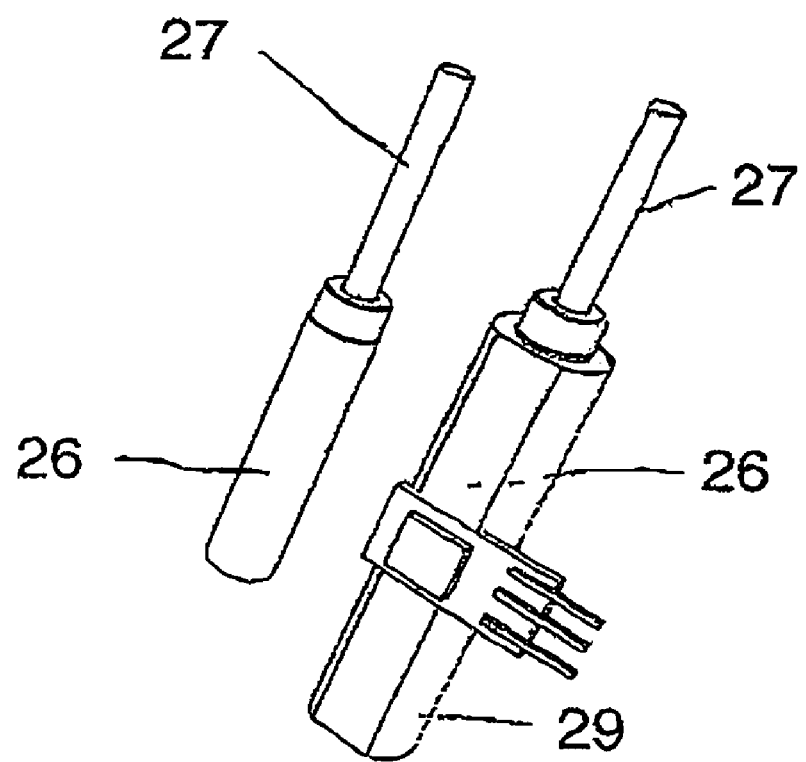
FIG. 4 is a perspective view of the Hall effect displacement measuring assembly used in the embodiment of FIG. 2, and of a magnet and mounting shaft thereof.

FIG. 4 illustrates a Hall effect displacement measuring assembly 25 comprising a magnet assembly with a magnet 26 and mounting shaft 27 attached thereto. In the illustrated embodiment, the axis along which the magnet 26 can move in relation to a Hall effect transducer 28 is dictated by a magnet guide 29 which is embodied here as a tubular structure, a lumen of which is large enough to permit insertion of the magnet 26 therein. The magnet guide 29 is oriented such that the axis of movement of the magnet is parallel to the walls of the casing members 9, 10.

The data acquisition system is operative to record the displacement distance as the displacement distance changes over a time period. Calibration of the springs 13 allows correlation between displacement, measured by the Hall effect displacement measuring assembly 25, and force thus allowing calculation of the displacement force as the displacement force changes over the time period.

Figure 5:
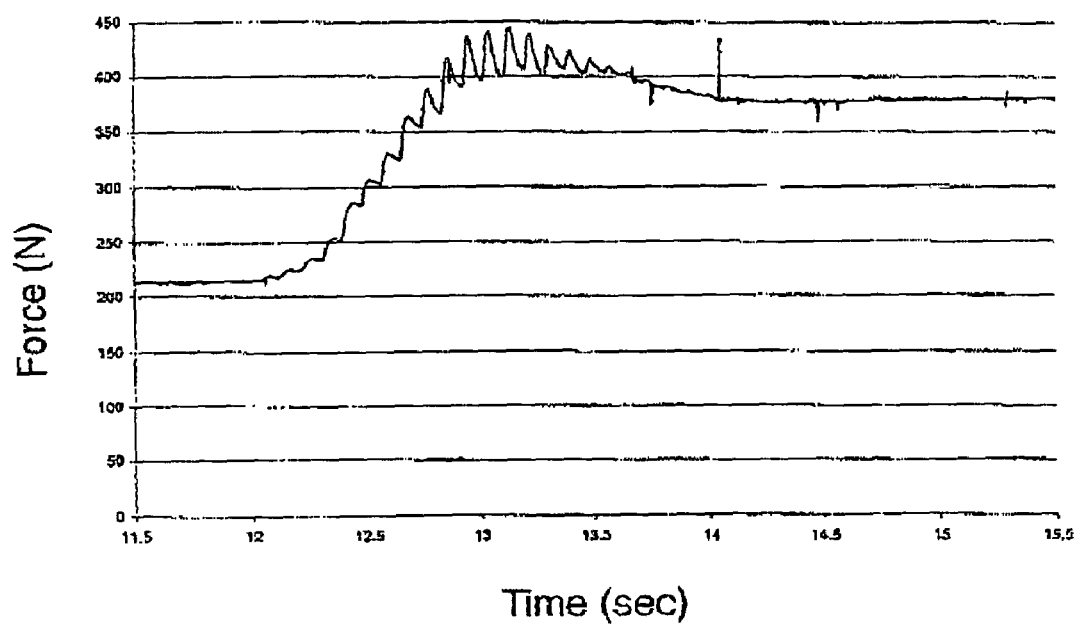
FIG. 5 illustrates a temporal force profile representing output from the Hall effect displacement measuring assembly of the embodiment of FIG. 2 when subjected to a displacement force.

An apparatus substantially as illustrated in FIGS. 2 and 3 was inserted in soil below the surface thereof. The surface of the soil was impacted using a flailing-hammer-type landmine detonation device. Output from the Hall effect transducer, representing a temporal force profile is illustrated in FIG. 5 wherein displacement of the upper plate 3 in relation to the base 7 is expressed as force as a function of time. Calibration of the springs 13 allows correlation between displacement, measured by the Hall effect displacement measuring assembly 25, and force.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

We claim:

1. A method of measuring the displacement of, and force on, visco-elastoplastic media below a surface thereof, the method comprising:

providing an upper plate having a top surface, and a base and locating the base and upper plate at a desired depth under the surface of the visco-elastoplastic media;

orienting the upper plate relative to the base such that a displacement force exerted on visco-elastoplastic media above the top surface will move the upper plate a displacement distance downward toward the base;

with guides, maintaining the upper plate and the base in alignment such that movement of the upper plate toward the base is along a displacement axis;

providing a calibrated bias element operative to exert a calibrated bias force resisting movement of the upper plate toward the base;

exerting a load force on the visco-elastoplastic media and measuring the displacement distance moved by the upper plate towards the base in response to the load force; and recording the displacement distance, and calculating the displacement force exerted on the top surface of the upper plate required to move the upper plate the displacement distance against the calibrated bias force.

2. The method of claim 1 wherein the calibrated bias element comprises a spring having a known spring constant such that the displacement force required to move the upper plate through the displacement distance toward the base can be calculated.

3. The method of claim 1 further comprising limiting the displacement distance.

4. The method of claim 1 further comprising measuring movement of the base along the displacement axis with respect to the visco-elastoplastic media with an accelerometer attached to the base.

5. The method of claim 1 wherein the guides comprise an upper casing member telescoping with respect to a lower casing member, and wherein the upper plate is fixed to the upper casing member and the base comprises the lower case member.

6. The method of claim 1 wherein the visco-elastoplastic media is soil.

7. The method of claim 1 wherein the displacement distance is measured with a Hall effect displacement measuring assembly comprising a magnet fixed to one of the upper plate and the base, and a Hall effect transducer fixed to the other of the upper plate and the base.

8. The method of claim 7 further comprising recording the displacement distance as the displacement distance changes over a time period.

9. The method of claim 8 further comprising calculating the displacement force as the displacement force changes over the time period.

10. An apparatus for measuring the displacement of, and force on, visco-elastoplastic media below a surface thereof, the apparatus comprising:

an upper plate having a top surface and mounted in the apparatus such that a displacement force exerted on the top surface by visco-elastoplastic media above the upper plate will move the upper plate a displacement distance downward toward a base;

guides operative to maintain the upper plate and the base in alignment such that movement of the upper plate toward the base is along a displacement axis;

a calibrated bias element operative to exert a calibrated bias force resisting movement of the upper plate toward the base;

a displacement measuring device operative to measure the displacement distance moved by the upper plate towards the base, and operative to generate a movement signal corresponding to the displacement distance; and a data acquisition system operative to receive and record the movement signal, and operative to calculate the displacement force exerted on the top surface of the upper plate required to move the upper plate the displacement distance against the calibrated bias force; wherein an area between the upper plate and the base is substantially sealed to prevent entry of visco-elastoplastic media into the area when the apparatus is buried in the visco-elastoplastic media.

11. The apparatus of claim 10 wherein the calibrated bias element comprises a spring having a known spring constant such that the displacement force required to move the upper plate through the displacement distance toward the base can be calculated.

12. The apparatus of claim 10 further comprising a displacement limiting assembly operative to limit the displacement distance.

13. The apparatus of claim 10 further comprising an accelerometer attached to the base, and operative to measure movement along the displacement axis of the base with respect to the visco-elastoplastic media.

14. The apparatus of claim 10 wherein the guides comprise an upper casing member telescoping with respect to a lower casing member, and wherein the upper plate is fixed to the upper casing member and the base comprises the lower casing member.

15. The apparatus of claim 10 wherein the visco-elastoplastic media is soil.

16. The apparatus of claim 10 wherein the displacement measuring device comprises a Hall effect displacement measuring assembly.

17. The apparatus of claim 16 wherein the Hall effect displacement measuring assembly comprises a magnet fixed to one of the upper plate and the base, and a Hall effect transducer fixed to the other of the upper plate and the base.

18. The apparatus of claim 17 wherein the data acquisition system is further operative to record the displacement distance as the displacement distance changes over a time period.

19. The apparatus of claim 18 wherein the data acquisition system is further operative to calculate the displacement force as the displacement force changes over the time period.

* * * * *